United States Patent [19]

Meltzer

[11] 4,143,116

[45] Mar. 6, 1979

[54] CONTACT LENS STERILIZING APPARATUS

[75] Inventor: Robert J. Meltzer, Williamsville, N.Y.

[73] Assignee: American Optical Corporation, Southbridge, Mass.

[21] Appl. No.: 715,593

[22] Filed: Aug. 18, 1976

[51] Int. Cl.² .................... A61L 3/00; A61L 13/00
[52] U.S. Cl. .................... 422/116; 74/3.5; 422/117; 422/211; 422/236; 422/292
[58] Field of Search .............. 21/58, 83, 84, 91; 74/3.5; 119/51.11, 51.14, 51.15

[56] References Cited

U.S. PATENT DOCUMENTS

| 3,754,527 | 8/1973 | Jenkins | 119/51.14 |
|---|---|---|---|
| 4,013,410 | 3/1977 | Thomas et al. | 21/58 |

Primary Examiner—Morris O. Wolk
Assistant Examiner—Arnold Turk
Attorney, Agent, or Firm—Jeremiah J. Duggan; Alan H. Spencer

[57] ABSTRACT

Contact lens sterilizer has a timer operating a catch for holding a capsule containing contact lenses in sterilizing solution in a sterilizing position. In this position, the capsule is inclined toward inversion. When the timer releases the catch after a predetermined period of time, the capsule swings to a substantially inverted position. In this position, a catalyst contained in one end of the capsule contacts the sterilizing solution to neutralize the same. Optionally, a lock mechanism prevents removal of the capsule from the sterilizer until neutralization is complete.

8 Claims, 7 Drawing Figures

CONTACT LENS STERILIZING APPARATUS

BACKGROUND OF THE INVENTION

The present invention relates to a contact lens sterilizing apparatus and more particularly to a timing apparatus for controlling the duration of sterilization and automatically initiating neutralization thereof.

U.S. Pat. No. 3,912,451, issued Oct. 14, 1975, describes a method for sterilizing contact lenses using hydrogen peroxide and neutralizing the hydrogen peroxide with a catalyst.

The present invention is directed to a timing apparatus for effecting contact lens sterilization by a method such as that described by the aforementioned patent.

BRIEF DESCRIPTION OF THE PRESENT INVENTION AND DRAWINGS

The sterilizing apparatus, according to the present invention, has a timing motor operably connected to a catch. The catch holds a pivotably-mounted capsule for receiving contact lenses and solution in a sterilizing position. Pivot members located at one end of the capsule engage a pivot mount on the sterilizer. The catch holds the capsule in a first position either inclined or tended toward inversion with the sterilizing solution in contact with the lenses. After a predetermined period of time, the catch releases the capsule and the capsule swings to a substantially inverted position. In the inverted position, contact is effected between the sterilizing solution and a neutralizer located at the other end of the capsule. Optionally, lock members prevent removal of the capsule from the apparatus until sufficient time has passed to complete the neutralization of the sterilizing solution.

THE PREFERRED EMBODIMENT

Figure 5:
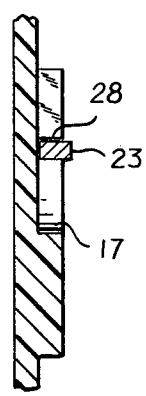
FIG. 5 is an enlarged view along section 5—5 of FIG. 2.
Figure 1:
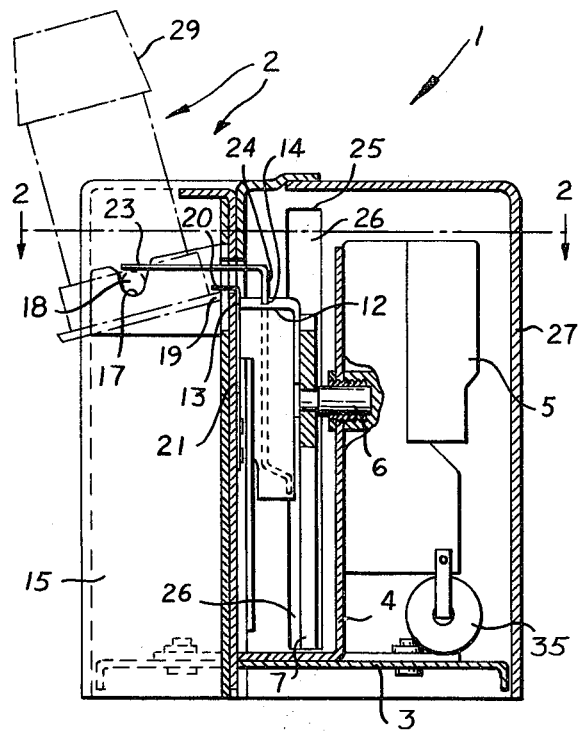
FIG. 1 is a side view of the preferred embodiment shown partly in section.
Figure 2:
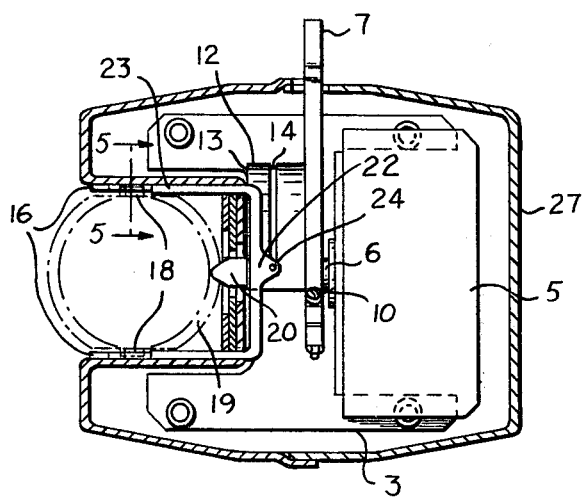
FIG. 2 is a top view of the preferred embodiment shown partly in section.
Figure 3:
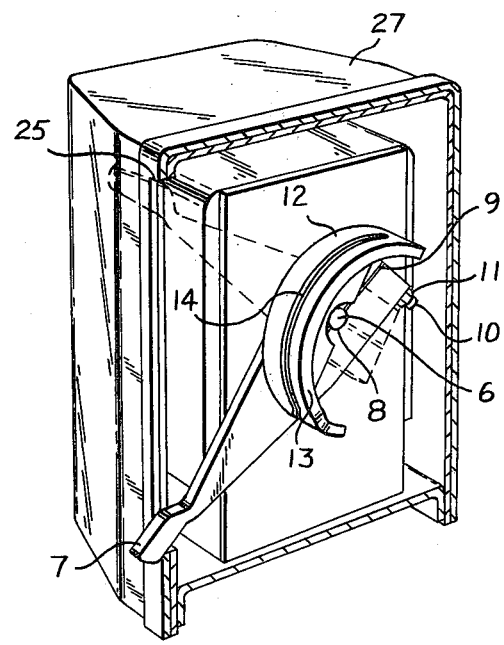
FIG. 3 is a front perspective view with the cam and lever exposed.
Figure 4:
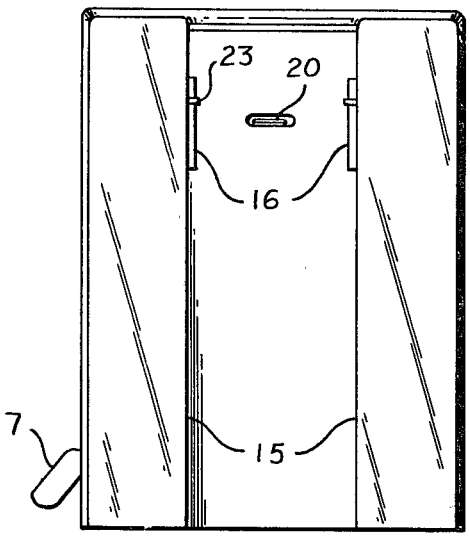
FIG. 4 is a front view of the preferred embodiment.
Figure 7:
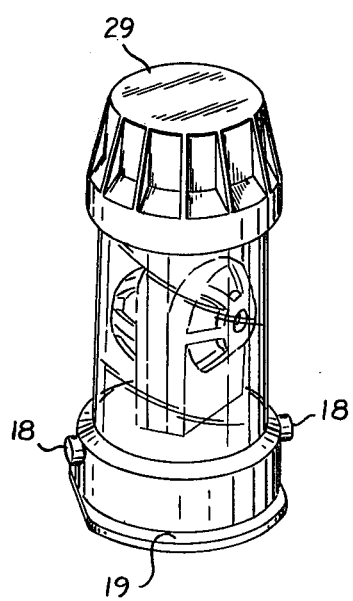
FIG. 7 is an illustration of a suitable capsule.

Referring to FIG. 1, the sterilizer is generally indicated by 1. Capsule 2 is shown dotted in the sterilizing position. A base 3 carries motor support 4 locating motor 5 with shaft 6 horizontally positioned. Motor 5 can be any type of timing motor. A preferred type of motor is a clock motor powered by battery 35 which provides the convenience of portability without reliance on electrical outlets. However, either an electric or windup motor could be used. Lever 7 has bore 8 adapted to receive shaft 6. Slot 9 permits adjustment of bore 8 through bolt 10 and nut 11. The diameter of bore 8 is adjusted to permit shaft 6 to slip inside bore 8 when lever 7 reaches end 25 of opening 26 in case 27 or when lever 7 is manually moved in a counterclockwise direction. Cam 12 is fastened to lever 7 and has a cam edge 13 and cam groove 14. Case 27 has recessed side walls 15 with pivot mounts 16 as shown in FIG. 4. Recesses 17 are adapted to receive pins 18 located at one end of capsule 2 as shown in FIG. 7. Capsule 2 also has lip 19 for engagement with catch 20. Resilient portion 21 of catch 20 biases catch 20 against cam edge 13.

Lock 22 has fingers 23 which slide in grooves 28. Pins 18 are held in recesses 17 when the lock fingers 23 are in the position shown in FIG. 1 to prevent patient removal of capsule 2 during sterilization and neutralization. Lock 22 has pin 24 operatively engaging cam groove 14 for sliding lock fingers 23 away from recesses 17 to permit removal of capsule 2 after neutralization is complete.

In practice, the sterilizer is used by partially filling capsule 2 with a sterilizing solution. Cap 29 of capsule 2 contains a neutralizer (not shown) and is placed on capsule 2 after lenses and solution have been inserted into the capsule. Either a catalytic neutralizer, such as that disclosed in U.S. Pat. No. 3,912,451 or a chemical neutralizer can be used. Capsule 2 is then placed in sterilizer 1 in a substantially vertical position using care to avoid contacting the sterilizing solution with the neutralizer. While the capsule is held in a substantially vertical position, lever 7 is manually depressed to the position shown in FIG. 4. Depression of lever 7, which is permitted by slippage of bore 8 around shaft 6, rotates cam 12 in a counterclockwise direction. Catch 20 is moved by cam edge 13 into engagement with lip 19 and lock fingers 23 are moved by pin 24 and cam groove 14 into the position over recesses 17 as shown in FIG. 1. When lever 7 is released, the frictional engagement of bore 8, with motor shaft 6, slowly drives cam 12 in a clockwise direction.

Figure 6:
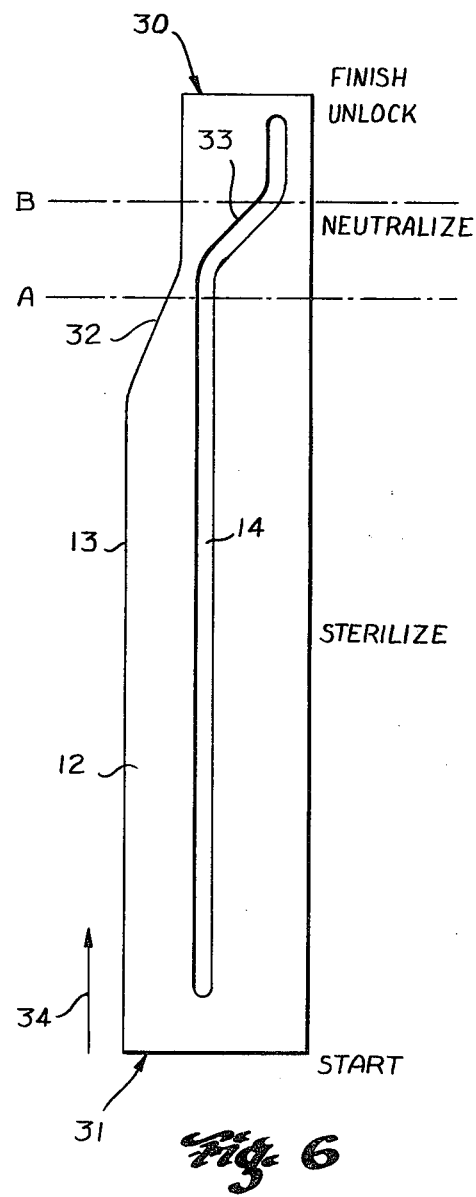
FIG. 6 is a displacement diagram of the cam.

Referring to FIG. 6, the cam displacement diagram is used for illustrating typical timer sequence. End 30 represents the finish of cycle position and end 31 represents the start of the cycle position. The process steps are identified as the sterilize, neutralize and unlock zones. As lever 7 is depressed, cam edge 13 forces catch 20 into engagement with lip 19. Since catch 20 is biased against cam edge 13, curve 32 in cam edge 13 represents the transition portion of cam edge 13 where catch 20 moves into engagement with lip 19 when the lever is depressed and releases lip 19 as the cam rotates clockwise when driven by timer motor 5. Lock fingers 23 are slid over capsule pins 18 as curve 33 of groove 14 passes pin 24 when the lever is being depressed. When lever 7 is released, the cam travels clockwise in the direction indicated by arrow 34 in FIG. 6. When position A on curve 32 reaches catch 20, lip 19 of capsule 2 is released by catch 20 and capsule 2 swings to a substantially inverted position. Contact between the sterilizing solution and the neutralizer in cap 29 is effected by substantial inversion of capsule 2. Lock 22 prevents removal of capsule 2 until curve 33 retracts fingers 23 when pin 24 is reached by position B of cam 12. This completes a sterilization cycle and the capsule with the contact lenses may then be removed.

I claim:

1. A sterilizer for contact lenses which comprises, a frame having capsule mounting means, a capsule for receiving contact lenses and a sterilizing solution having a neutralizer near one end and having pivot means near the other end, said pivot means being adapted to pivotally cooperate with said mounting means, catch means for releasably holding said capsule in a treating position with a major portion of the capsule above said pivot means to immerse contact lenses in a sterilizing solution while said neutralizer is disposed above and out of contact with said sterilizing solution said mounting means holding said capsule tended toward inversion for neutralization when in said position, timing means operably connected to said catch for releasing said capsule to swing about said pivot means to a substantially inverted position and effect contact between said solution and neutralizer.

2. The sterilizer according to claim 1 wherein said mounting means includes means for maintaining the capsule in an inclined position whereby the force of gravity swings said capsule toward the inverted position upon release of said capsule by said catch means.

3. The sterilizer according to claim 1 wherein said timing means includes a motor, a cam driven by said motor, said cam engaging said catch for first moving said catch to hold said capsule in the treating position and then permitting said catch to move to a position of disengagement from said capsule to release said capsule from said treatment position.

4. The sterilizer according to claim 3 wherein said catch is biased against said cam, said motor is a battery-powered clock motor having a shaft and said cam is frictionally coupled to said shaft to permit said cam to be forceably rotated counterclockwise about said shaft against said frictional coupling.

5. The sterilizer according to claim 1 further including lock means for preventing removal of said capsule prior to neutralization of the sterilizing solution.

6. The sterilizer according to claim 5 wherein said lock means temporarily prevent said pivot means includes means to from being removed from said mounting means.

7. The sterilizer according to claim 1 wherein
said timing means includes a battery-powered clock motor, a cam frictionally coupled for rotation by said motor, said cam having a start position and rest position, means to forceably rotate said cam counterclockwise from said rest position to said start position against said frictional coupling, said cam having a cam edge and a cam groove,
said catch means includes a catch and biasing means to urge said catch against said cam edge,
said capsule mounting means including a pair of spaced-supports, each said support having a recess, each said recess having an entrance,
said pivot means including a pair of diametrically-opposed, cylindrical pins adapted to engage a respective recess through said entrance for supporting said capsule, and
lock means for preventing removal of said capsule prior to neutralization of said sterilizing solution, said lock means including a pair of protruding members slideably mounted in said spaced-supports, a follower connected to said protruding members and adapted to engage said cam recess to cover said entrances when said cam is moved to said start position.

8. The sterilizer according to claim 1 wherein the neutralizer is a catalytic neutralizer.

* * * * *